(12) United States Patent
Bauerfeind et al.

(10) Patent No.: US 8,579,843 B2
(45) Date of Patent: Nov. 12, 2013

(54) KNEE JOINT BANDAGE

(75) Inventors: Hans H. Bauerfeind, Zeulenroda (DE);
Wolfgang Krause, Hofbieber (DE);
Heinrich Hess, Kleinblittersdorf (DE);
Rainer Scheuermann, Rainsdorf (DE)

(73) Assignee: Bauerfeind AG, Zeulenroda (DE)

( * ) Notice: Subject to any disclaimer, the term of this patent is extended or adjusted under 35 U.S.C. 154(b) by 119 days.

(21) Appl. No.: 12/520,725

(22) PCT Filed: Dec. 19, 2007

(86) PCT No.: PCT/EP2007/011218
§ 371 (c)(1),
(2), (4) Date: Sep. 3, 2009

(87) PCT Pub. No.: WO2008/077571
PCT Pub. Date: Jul. 3, 2008

(65) Prior Publication Data
US 2010/0036303 A1    Feb. 11, 2010

(30) Foreign Application Priority Data
Dec. 22, 2006   (DE) .......................... 10 2006 061 060

(51) Int. Cl.
*A61F 5/00* (2006.01)
(52) U.S. Cl.
USPC .................. 602/26; 602/23; 602/62; 602/63; 602/75
(58) Field of Classification Search
USPC ................. 602/23, 26, 62, 63.75, 60, 61, 20; 128/846, 869, 878, 882, 892; 606/201, 606/203, 204; 2/22, 23, 24, 25, 26, 62, 455
See application file for complete search history.

(56) References Cited

U.S. PATENT DOCUMENTS

| 329,815   | A |   | 11/1885 | Hawkins |
|-----------|---|---|---------|---------|
| 2,818,571 | A | * | 1/1958  | Grant ................................... 2/22 |
| 4,425,912 | A | * | 1/1984  | Harper ............................ 602/26 |
| 4,445,505 | A | * | 5/1984  | Labour et al. ................... 602/26 |
| 5,016,621 | A | * | 5/1991  | Bender ............................ 602/26 |
| 5,024,216 | A | * | 6/1991  | Shiono ............................ 602/26 |

(Continued)

FOREIGN PATENT DOCUMENTS

| EP | 0 329 815 A1 |   | 8/1989  |
|----|--------------|---|---------|
| EP | 329815 A1    | * | 8/1989  |
| EP | 0 396 702 B1 |   | 11/1990 |
| EP | 1 629 811 A1 |   | 3/2006  |

*Primary Examiner* — Patricia Bianco
*Assistant Examiner* — Caitlin Carreiro
(74) *Attorney, Agent, or Firm* — Birch, Stewart, Kolasch & Birch, LLP

(57) ABSTRACT

A knee joint bandage made of elastic textile material having a profiled insert encompassing the kneecap in a recess, the insert being covered by an overlay fastened to the textile material. Within the profile insert is a flexible, non-expandable tensioning member for connecting the regions of the kneecap poles on the fibula side in an arc around the kneecap wherein the distance between these regions increases during bending of the knee joint, the distance of the arc from the connecting line of the knee poles is decreased, and the tensioning member presses on the adjacent side of the kneecap, displacing the same medially and centering it. The bandage is provided with a flexible tensioning band, which partially covers the kneecap in its peripheral area relative to the tensioning member, the tensioning band substantially extends in the direction between the kneecap poles such that it counteracts a lifting of the kneecap.

5 Claims, 2 Drawing Sheets

(56) References Cited

U.S. PATENT DOCUMENTS

| | | | |
|---|---|---|---|
| 5,411,037 A | * | 5/1995 | Hess et al. .................... 128/882 |
| 5,613,943 A | * | 3/1997 | Palumbo ......................... 602/62 |
| D444,563 S | * | 7/2001 | Rodgers ....................... D24/190 |
| 7,517,331 B2 | * | 4/2009 | Reinhardt et al. .............. 602/61 |
| 2006/0041214 A1 | * | 2/2006 | Reinhardt et al. .............. 602/60 |

* cited by examiner

KNEE JOINT BANDAGE

CROSS-REFERENCE TO RELATED APPLICATIONS

The present application claims priority under 35 USC 119 to PCT Patent Application No. EP2007/011218 filed on Dec. 19, 2007 which claims priority to German Patent Application No. 10 2006 061 060.1 filed on Dec. 22, 2006 the entire contents of which are hereby incorporated by reference.

BACKGROUND OF THE INVENTION

1. Field of the Invention

The invention relates to a knee joint bandage made of elastic textile material, the bandage being provided with an oval-shaped profiled insert encompassing the kneecap in an opening, the profiled insert being covered by an overlay, which is fastened to the textile material and is made of identical or similar textile material. Arranged within the profiled insert is a flexible, non-expandable tensioning member extending between the kneecap poles on the fibula side in an arc around the kneecap, such that during bending of the knee joint, a distance of the tensioning member from the connection line of the kneecap poles is decreased, and the tensioning member presses on an adjacent side of the kneecap, displacing the same medially and centering it.

2. Description of Background Art

A knee joint bandage such as this is disclosed in EP 396 702 B1. In this knee joint bandage, lateral pressure is exerted on the kneecap during bending of the knee joint, that is, in the direction of the internal side of the knee joint. It has been found that with a slight and desired displacement of the kneecap brought about in this way, the side of the kneecap facing away from the tensioning member lifts lightly off the knee joint, especially when a corresponding deformation of the bones in the knee joint is already present (for example, due to some pre-existing condition). In a worst case scenario, this can result in the dislocation of the kneecap from its normal position.

SUMMARY AND OBJECTS OF THE INVENTION

It is the object of an embodiment of the invention to improve the conventional knee joint bandage such that while retaining the desired effect of the tensioning member, any potential displacement of the kneecap away from the knee joint is prevented. According to the embodiment of the invention, this is done by providing the bandage in the region of the kneecap with a flexible tensioning band, which partially covers the kneecap, with the tensioning band extending substantially in the direction between the kneecap poles such that it counteracts a lifting of the kneecap.

As a result of the tensioning band extending across the kneecap and thereby partially covering the kneecap, instant pressure is exerted on the affected region of the kneecap as soon as the kneecap shows any tendency of lifting off the joint. In this instance, the non-elastic tensioning band acts, in a manner of speaking, as a movement limiter, for the corresponding side of the kneecap so that laterally, it can be marginally displaced from the tensioning member but is prevented by the tensioning band from thereby lifting off the knee joint. This is a technically simple but functionally important additional structural design of the knee joint bandage, which merely in the region of the kneecap requires the addition of the aforementioned tensioning band.

The previously described knee joint bandage can be combined in a beneficial manner with a femoral bandage, which adjoins the knee joint bandage, and, in a manner of speaking, is a continuation thereof, wherein a pelotte is inserted into the femoral bandage extending in the longitudinal direction of the bandage and featuring transversal ribs, the ribs being separated by likewise transversal notches. With a pelotte such as this, by pressing the corresponding bandage on a muscle located therebelow, a relaxing of said muscle can be achieved, which is of particular importance if the muscle is responsible for a dislocation of the kneecap. In other words, the pelotte with its transversal ribs ensures that by relaxing the muscle in question, the strength for moving the kneecap is decreased.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
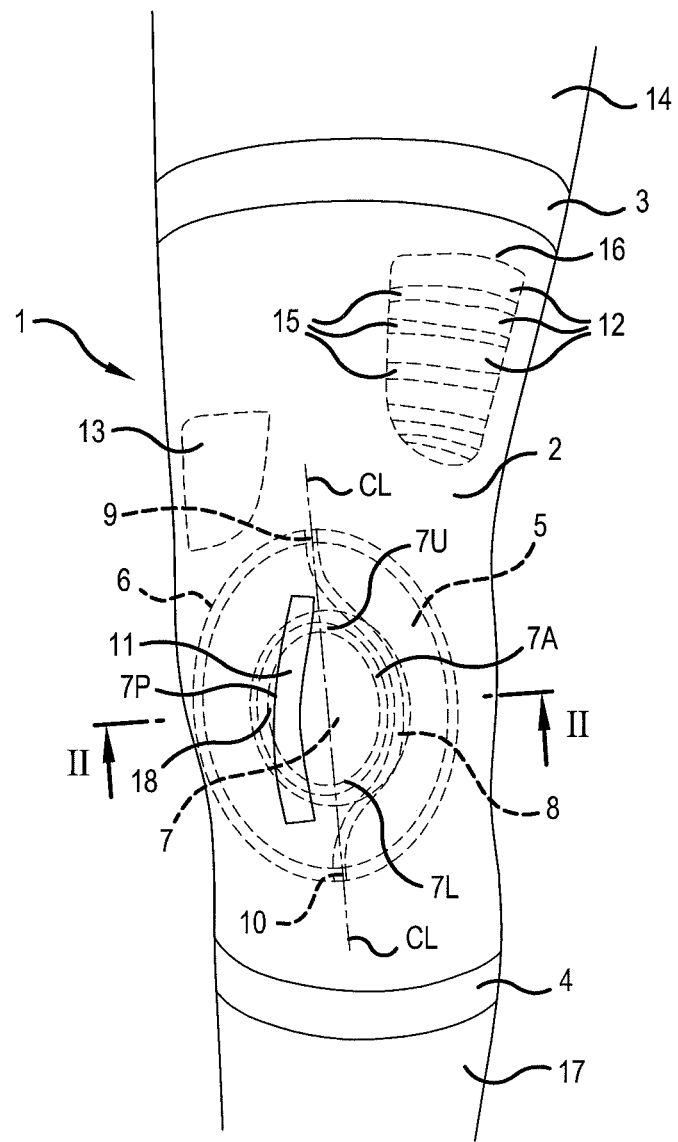
FIG. 1 shows a bandage extending across the knee joint from the thigh to the lower leg.
Figure 2:
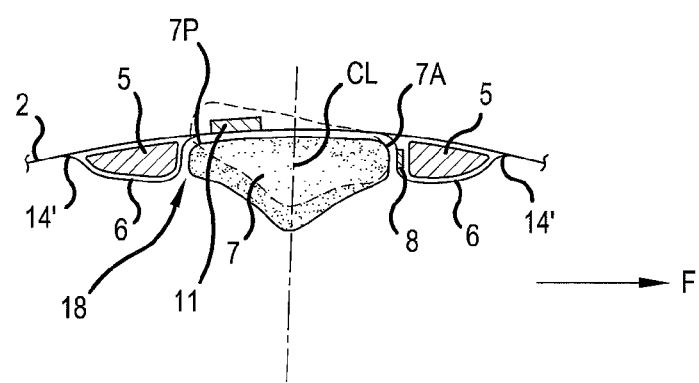
FIG. 2 shows a cross section along line II-II of FIG. 1.

FIG. 1 illustrates bandage 1, which extends from thigh 14 to lower leg 17 and is made of an elastic textile material 2. To facilitate its application and removal, strips 3 and 4 are attached to upper and lower longitudinal ends of bandage 1, the strips 3 and 4 being made of longitudinally elastic material forming a non-fraying edge at each end of bandage 1. In the region of the knee joint, bandage 1 is of a special structural design, which counteracts a lateral displacement of kneecap 7 during bending of the knee. For this purpose, bandage 1 has an oval-shaped profiled insert 5 having an opening 18. The opening 18 in the central portion of the oval-shaped profiled insert 5 encompasses the kneecap 7 in a manner such that the oval-shaped profiled insert 5 surrounds the lateral side edges of the kneecap 7. The profiled insert 5 is provided with an overlay 6 which is formed over the profiled insert 5. Enclosed in the overlay 6 of the profiled insert 5 is the flexible, but non-expandable, tensioning member 8, which at its ends 9 and 10 is firmly attached to the profiled insert 5. If the leg illustrated in a straightened position is bent, the bandage 1 expands in the region of the knee joint causing the ends 9 and 10 of tensioning member 8 to separate from one another. In other words. When the leg is bent, the distance between ends 9 and 10 of the non-expandable, tensioning member 8 increases. As a result, the tensioning member 8 is displaced inwardly from its illustrated position in the direction of the kneecap 7. Thus, in the region of the knee joint, the tensioning member 8 of the bandage 1 counteracts the tendency of the kneecap 7 to slip towards the right (toward the right side of FIGS. 1 and 2), that is, in the direction of the arc-shape of the tensioning member 8, which in the framework of a defective function of the knee joint happens frequently. This effect is countermanded by the pressure exerted by the tensioning member 8 on the kneecap 7. To prevent a lifting of the kneecap 7 on the side (left side in FIGS. 1 and 2) that faces away from the tensioning member 8, the bandage 1 is provided with the flexible tensioning band 11 (in the form of a rectangular strip) in the region of the kneecap 7, which partially covers an outward facing portion 7P of the kneecap 7 on a lateral side of a connection line CL of the kneecap poles 7U, 7L that is opposite relative to a side where the tensioning member 8 is located. As can be seen in FIG. 2, the oval-shaped profiled insert 5 is provided on an underside of the elastic textile material 2, and has the opening 18 for accommodating a kneecap 7 in a manner such that the oval-shaped profiled insert 5 surrounds the lateral side edges of the kneecap 7 when the person is wearing the bandage 1. The profiled insert 5 is entirely covered by overlay 6, is fastened to the elastic textile material 2 and is made of a material that is substantially identical to the elastic textile material 2. The flexible, non-expandable tensioning member 8 is arranged in the oval-shaped profiled insert 5 extending from above an upper kneecap pole 7U to below a lower kneecap pole 7L on a fibula side F. The flexible, non-expandable tensioning member 8 has an arc-shape and extends around a lateral side edge 7A of the kneecap 7, such that during bending of a knee joint of the person wearing the bandage, a distance of the flexible, non-expandable tensioning member from the connection line CL of the kneecap poles 7U, 7L decreases, and the non-expandable tensioning member 8 presses on a lateral side edge 7A of the kneecap 7 adjacent to the non-expandable tensioning member 8, displacing the kneecap 7 medially, in order to center the kneecap 7. A flexible tensioning band 11 (in the form of a rectangular strip) provided on an outer side of the elastic textile material 2, and is arranged entirely on one lateral side of the connection line CL opposite to where the non-expandable tensioning member 8 extends along the lateral side edge 7A of the kneecap 7, and partially covers the outward facing portion 7P of the kneecap 7 on the one lateral side of the connection line CL opposite to where the non-expandable tensioning member 8 extends along the lateral side edge 7A of the kneecap 7. In other words, the flexible tensioning band 11 (in the form of a rectangular strip) is provided entirely on the side of the kneecap 7 furthest away from the non-expandable tensioning member 8. Further, the flexible tensioning band 11 (in the form of a rectangular strip) has a longest dimension which is shorter than a vertical dimension of the oval-shaped profiled insert 5, wherein the single, flexible tensioning band extends directly and continuously in a lengthwise direction of the knee joint bandage 1 from a position above the upper kneecap pole 7U to below the lower kneecap pole 7L. As a result, the flexible tensioning band 11 extends continuously in the lengthwise direction of the bandage 1 directly over the outward facing portion 7P of the kneecap 7 accommodated in the opening 18, such that the flexible tensioning band 11 counteracts a lifting of the outward facing portion 7P of the kneecap 7 accommodated in the opening 18, such that the flexible tensioning band 11 counteracts a lifting of the kneecap 7 when the distance of the flexible, non-expandable tensioning member from the connection line CL of the kneecap poles 7U,7L decreases.

This arrangement of the tensioning band 11 is described in more detail with reference to the cross-sectional drawing according to FIG. 2. Additionally, FIG. 2 illustrates the particular parts of the oval-shaped profiled insert 5. As can be seen in FIG. 2, the oval-shaped profiled insert 5 has an opening 18 and the kneecap 7 is encompassed (accommodated) in the opening 18. Furthermore, FIG. 2 illustrates in a sectional view the flexible tensioning band 11 preventing the lifting of the kneecap 7. In addition, FIG. 2 shows fastening points 14', by which the overlay 6 is fastened to the elastic textile material 2 of the bandage 1. In addition, FIG. 1 shows that the flexible tensioning band 11 is arranged entirely on one lateral side of the connection line CL of the kneecap poles 7U, 7L, and the tensioning member 8 is arranged on an opposite lateral side of the connection line CL of the kneecap poles 7U,7L.

In the region between strip 3 and the oval-shaped profiled insert 5 (see further below) encompassing the kneecap 7, a pelotte 16 is fastened from the inside to the elastic textile material 2 of bandage 1, by adhesive, for example. The pelotte 16 is attached at a place in an area of the thigh, where thigh muscles to be treated are located, onto which pressure needs to be exerted in a certain way. Pelotte 16 includes transversal ribs 12 which are separated from one another by notches 15, which also extend in a transversal direction. During the bending of the knee, the structural design of pelotte 16 has a muscle-relaxing effect, because pelotte 16 exerts pressure only via the transversal ribs 12, extending separately from one another, onto the muscles located therebelow, which react to such treatment by relaxing internally. In this way, the desired therapeutic effect of the bandage 1 is achieved by means of pelotte 16. In the illustrated exemplary embodiment, pelotte 16 has five such transversal ribs 12 separated from one another by four transversally extending notches 15. Furthermore, with respect to the effect of pelotte 16, reference is made to a parallel application filed by the same Applicant and having the same filing date, and having the Application No. DE B109178, in which the structural design of the pelotte 16 is described in detail.

The arrangement of pelotte 16 designed as described does not prevent additional pelottes from being attached to other parts of bandage 1, for example, pelotte 13, which in the conventional way exerts constant pressure on the muscles located therebelow. Thus, the bandage 1 can have one of, or a plurality of, specially designed pelottes 16 as well as additional pelottes according to the design of pelotte 13.

It has been shown that the tendency of a lateral displacement of kneecap 7 is further reduced by the specially constructed muscle-relaxing pelotte applied to thigh muscles responsible for the displacement of kneecap 7, which enhances the effect of the flexible, non-expandable tensioning member 8 discussed above. With tensioning member 8 and pelotte 16, an especially intensive impact on the proper position of the kneecap 7 is achieved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:
1. A knee joint bandage comprising:
  an elastic textile material for surrounding a portion of a leg of a person from an intermediate portion of a thigh to an intermediate portion of a lower leg,
  an oval-shaped profiled insert having an opening for accommodating a kneecap of a person such that the oval-shaped profiled insert surrounds the kneecap of the person when wearing the knee joint bandage,
  an overlay made of material that is identical or similar to the elastic textile material wherein the overlay covers the oval-shaped profiled insert and the oval-shaped profiled insert is fastened to an underside of the elastic textile material, so that when the person is wearing the knee joint bandage, the opening encompasses a kneecap of the person, and a flexible, non-expandable tensioning member arranged in the oval-shaped profiled insert wherein the flexible, non-expandable tensioning member extends from above an upper kneecap pole to below a lower kneecap pole and has an arc-shape and is positioned on a fibula side of the kneecap, such that, during bending of a knee joint, a distance from the flexible, non-expandable tensioning member to the fibula side of the kneecap deceases, and the flexible, non-expandable tensioning member presses on the fibula side of the kneecap, displacing the kneecap medially and centering the kneecap, the knee joint bandage further comprising:

a single, flexible tensioning band fastened on an outer side of the knee joint bandage so as to partially cover a portion of the kneecap on a side opposite to where the flexible, non-expandable tensioning member is located, wherein the single, flexible tensioning band is a rectangular strip that extends directly and continuously in a lengthwise direction of the knee joint bandage from above the upper kneecap pole over an outward facing portion of the kneecap that is exposed at the opening of the oval-shaped profiled insert and terminating below the lower kneecap pole such that the single, flexible tensioning band counteracts a lifting of the kneecap.

2. The knee joint bandage according to claim 1, wherein a portion of the knee joint bandage above the oval-shaped profiled insert includes a pelotte fastened to an inside of the elastic textile material of the knee joint bandage by adhesive, the pelotte having a long dimension extending in the lengthwise direction of the knee joint bandage, and ribs, which are separated from one another by notches, each of the ribs and the notches extending transversely relative to the long dimension of the pelotte and the lengthwise direction of the knee joint bandage.

3. The knee joint bandage according to claim 1, wherein the single flexible tensioning band has a length that is shorter than a length of the flexible, non-expandable tensioning member.

4. The knee joint bandage according to claim 2, wherein the pelotte is formed such that the ribs exert pressure onto thigh muscles of the person wearing the knee joint bandage.

5. The knee joint bandage according to claim 1, wherein a portion of the knee joint bandage above the oval-shaped profiled insert includes a pelotte having a long dimension extending in the lengthwise direction of the knee joint bandage, wherein the pelotte includes ribs, which are separated from one another by notches, each of the ribs and the notches extending transversely relative to the long dimension of the pelotte and the lengthwise direction of the knee joint bandage, the pelotte being formed such that the ribs exert pressure onto thigh muscles of the person wearing the knee joint bandage.

* * * * *